United States Patent [19]

Outlaw et al.

[11] Patent Number: 4,511,480

[45] Date of Patent: Apr. 16, 1985

[54] CORROSION INHIBITION IN DEEP GAS WELLS BY PHOSPHATE ESTERS OF POLY-OXYALKYLATED THIOLS

[75] Inventors: Benjamin T. Outlaw; Bernardus A. Oude Alink, both of St. Louis, Mo.; Joe A. Kelley, Collinsville, Ill.; Carol S. Claywell, St. Louis, Mo.

[73] Assignee: Petrolite Corporation, St. Louis, Mo.

[21] Appl. No.: 515,223

[22] Filed: Jul. 20, 1983

[51] Int. Cl.$^3$ .................... C23F 11/00; F17D 1/04
[52] U.S. Cl. .................... 252/8.55 E; 252/389 R; 260/925; 260/948; 260/949
[58] Field of Search ............ 252/8.55 B, 8.55 E, 252/389.21, 46.6; 106/14.12, 14.05; 260/948, 949, 925

[56] References Cited

U.S. PATENT DOCUMENTS

| | | | |
|---|---|---|---|
| 3,004,056 | 10/1961 | Nunn et al. | 260/948 |
| 3,326,919 | 6/1967 | Wakeman et al. | 260/925 |
| 3,488,289 | 1/1970 | Tate | 252/8.55 B |
| 3,965,003 | 6/1976 | Stanford et al. | 252/8.55 B |
| 4,138,346 | 2/1979 | Nassry et al. | 252/46.6 |

FOREIGN PATENT DOCUMENTS 951502  3/1964  United Kingdom .

OTHER PUBLICATIONS

Corrosion of Oil and Gas-Well Equipment—(1958)—American Petroleum Institute Publication 1-3,21,22,35,36,37,40,41,42,43,47,54,55.
Chemical Abstracts 61:2892a.

*Primary Examiner*—Veronica P. Hoke
*Attorney, Agent, or Firm*—Robert E. Wexler

[57] ABSTRACT

Phosphate esters of oxyalkylated thiols are used as corrosion inhibitors for ferrous metals in deep gas wells.

9 Claims, No Drawings

CORROSION INHIBITION IN DEEP GAS WELLS BY PHOSPHATE ESTERS OF POLY-OXYALKYLATED THIOLS

BACKGROUND OF THE INVENTION

1. Field of the Invention

This invention relates to the use of phosphate esters of oxyalkylated thiols as corrosion inhibitors.

More particularly, the invention relates to the inhibition of corrosion in steel, iron and other ferrous metals which are exposed to the hostile environments of gas wells, especially deep gas wells, and, especially, in such wells characterized as "sweet systems", i.e., where the environment comprises a high concentration of carbon dioxide.

Although a wide variety of corrosion inhibitors are known, they are not effective in all systems. For example, a corrosion inhibitor which is effective at low temperature, atmospheric pressure and neutral or slightly acidic conditions would not necessarily be effective at high temperature, high pressure and highly acidic conditions. The mechanism of corrosion within a system is so unique that, despite theoretical considerations, selection of corrosion inhibitors is often more empirical then deducible.

As primary oil and gas fields become depleted, deeper wells are drilled to tap new sources of petroleum and gas. Increased depth, however, poses increasingly severe corrosion problems. The conditions of, for example, deep gas wells place great corrosive stress upon the tubing and other equipment employed in such wells due to the highly oxidizing atmospheres and extreme temperature and pressure conditions. Thus, when the drilling cost of a well is in excess of $5-6 million, approximately half of which is tubing, the importance of effective corrosion inhibition becomes evident. When conventional oil or gas well corrosion inhibitors are employed in deep wells, they are often found to have little or no effectiveness, since they tend to degrade or volatilize and either lose effectiveness as a corrosion inhibitor or polymerize and clog the tubing.

It has now been found that phosphate esters of oxyalkylated thiols, used alone or in conjunction with other materials, are effective corrosion inhibitors for ferrous metals used in gas and oil wells, particularly in deep gas wells.

The corrosion inhibitors of the present invention are particularly effective in systems containing a high concentration carbon dioxide.

2. Prior Art

U.S. Pat. No. 3,004,056 discloses the preparation of phosphate esters of certain oxyalkylated thiols and discloses their utility as surface active agents.

SUMMARY OF THE INVENTION

The present invention relates to corrosion inhibition and to a class of phosphate ester compounds which have utility, either alone or in compositions comprising the same, as corrosion inhibitors for ferrous metals.

The compounds which have been found to be corrosion inhibitors for ferrous metals are phosphate esters of oxyalkylated thiols and the quaternaries and amine salts thereof.

Accordingly, the invention is directed to corrosion inhibiting compositions and to a process for inhibiting corrosion of ferrous metals.

DETAILED DESCRIPTION OF THE INVENTION

In accordance with the present invention, the compounds which have been found to have utility as corrosion inhibitors of ferrous metals are characterized by the following general formula:

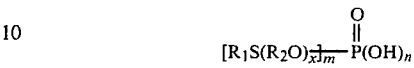

wherein $R_1$ represents alkyl, cycloalkyl, aryl, aralkyl and heterocyclyl; $R_2$ represents alkyl; x represents an integer of from 1 to about 4; m represents an integer which may be 1 or 2; n represents the integer 1 when m is 2 and represents 2 when m is 1.

The corrosion inhibiting compounds are prepared by oxyalkylation of a mercaptan and subsequent treatment of the oxyalkylate with a phosphating agent such as phosphorous pentoxide. The amount of alkylene oxide or equivalent which is reacted with the mercaptan starting material depends upon the product which one desires to obtain. Although other phosphating agents may be used in place of phosphorous pentoxide, the latter material offers best results.

The compounds used in accordance with this invention may be prepared by known methods, and especially in accordance with the general procedure set forth in U.S. Pat. No. 3,004,056 which describes a method for the oxyalkylation and phosphation of mercaptans to afford surface active agents, which procedure is incorporated herein by reference.

As described above, $R_1$ represents an alkyl radical of from about 4 to about 20 carbon atoms. Exemplary radicals represented by $R_1$ include butyl, amyl, hexyl, heptyl, octyl, isooctyl, nonyl, isononyl, decyl, isodecyl, undecyl, dodecyl, tridecyl, pentadecyl, octadecyl, eicosyl and the like and may be straight or branched chain.

Cycloalkyl radicals represented by $R_1$ include cyclopropyl, cyclobutyl, cyclopentyl, cyclohexyl and the like and may contain alkyl side chains.

Aryl radicals represented by $R_1$ include phenyl and substituted phenyl, e.g., tolyl, xylyl, mesityl, cumyl, ethylphenyl, octylphenyl, heptadecylphenyl, naphthyl, anthryl, phenananthryl and the like.

Aralkyl radicals represented by $R_1$ include benzyl, diphenylmethane, triphenylmethane and the like and may contain alkyl side chains.

Heterocyclyl groups represented by $R_1$ include cycloaliphatic and aromatic radicals containing at least one hetero atom (O, S, N) in the ring, e.g., furans, thiophenes, pyrroles, thiazoles, pyrazoles, oxazoles, pyrans, thiopyrans, pyridines, piperidines, oxazines, diazines, quinolines, phenanthridines and the like and may be alkylated.

Alkyl radicals included within the definition of $R_2$ include those having from 2 to about 4 carbon atoms, e.g., ethyl, propyl, and butyl.

The above-described radicals may also be substituted by groups known to those skilled in the art to assist corrosion inhibition and regulate solubility and filming characteristics. Thus the above-described compounds may be sulfonated, oxyalkylated, aminated, etc., according to methods well known in the art.

Preparation of the compounds used in the present invention may be represented by the following reaction equation:

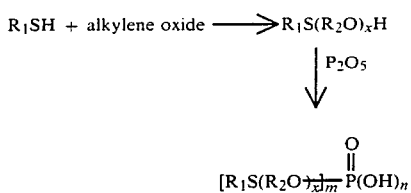

wherein $R_1$, $R_2$, x, m and n are defined above.

Mercaptans which may be used as starting materials to prepare the compounds described in accordance with the present invention include straight and branched chain mercaptans such as, butyl mercaptan, t-butyl mercaptan, octyl mercaptan, isooctyl mercaptan, nonyl mercaptan, decyl mercaptan, dodecyl mercaptan, tridecyl mercaptan, octadecyl mercaptan, eicosyl mercaptan, thiophenol, thiobenzol, thionaphthol and the like.

Oxyalkylating agents which may be used to prepare the corrosion inhibiting agents include any of the well known oxyalkylating agents, such as alkylene oxides, e.g., ethylene oxide, propylene oxide, butylene oxide and mixtures thereof. The oxyalkylation is conducted at a molar ratio of from about 0.25 to about 5, preferably from about 1 to about 5, especially from about 2 to about 3 moles oxyalkylating agent per mole of thiol. The degree of oxyalkylation is critical in determining solubility of the phosphate ester. Thus, the higher the degree of oxyalkylation, the more water soluble the phosphate ester will be. If the phosphate ester becomes too water soluble, it will tend to stay in solution rather than film out on the surface of the metal to be protected. Accordingly, the degree of oxyalkylation must be carefully regulated. The proper degree of oxyalkylation affording the best relative water/hydrocarbon solubility and corrosion inhibitory action must be determined empirically, since it will differ for each thiol being treated.

The corrosion inhibiting compounds may be added to a gas well neat or as a solution thereof in an appropriate solvent, e.g., hydrocarbon solvent, and may be used in combination with other materials well known in anti-corrosion formulations, e.g., surface active agents; film formers, e.g., dimer acids, solubilizing agents; demulsifiers, oxygen scavengers, e.g., hydrazine; biocides and the like.

Typical surface active agents which may be used in compositions comprising the corrosion inhibitors include anionic, cationic and nonionic types discussed in "Emulsion Theory and Practice", ACS Monograph No. 162, 1965, Reinhold Publishers, N.Y., particularly pages 221–226 thereof. Preferred surface active agents are the nonionic surfactants such as oxyalkylated alkylphenols, oxyalkylated fatty acids, oxyalkylated rosin acids, oxyalkylated fatty amines and cationic surfactants such as sulfonated naphthalenes.

Another aspect of the invention relates to the use of amine salts and quaternaries of the afore-described phosphate esters as corrosion inhibitors. Thus, the phosphate esters may be reacted with a wide variety of amines to afford the amine salts thereof. Typical amines with which the phosphate esters may be reacted include any amine which will react with a phosphate ester to fully or partially neutralize same. Such amines include the primary, secondary and tertiary aliphatic, alicyclic, aromatic and heterocyclic amines, e.g., alkylamines such as the mono-, di- and tri-methyl amines, propylamine, laurylamine, stearyl amine; alkanolamines, e.g., ethanolamine; cyclohexylamines; phenylamines; morpholinylamines; pyridylamines; ethoxylated amines, e.g., ethoxylated rosin amines; morpholines; pyridines; phenanthridines; aminoimidazolines; rosin amines; fatty acid amines, e.g., cocoanut fatty acid amines; alkyl sulfonamides; alkylbenzenesulfonamides; anilines; alkylene polyamines, e.g., ethylene diamine; polyalkyleneimines, e.g., polyethyleneimine and the like. The described amines are merely illustrative of the wide variety of amine which may be used to form salts of the phosphate esters of the invention. Obviously, one who is skilled in the art will readily determine other types of amines which may be utilized in a functionally equivalent manner. The amine salts of the phosphate esters may be converted to the corresponding quaternaries by well known methods with alkyl and aromatic halides, e.g., methyl iodide, benzyl chloride.

The amine salts and quaternaries of the phosphate esters provide water dispersability and film forming characteristics while retaining the hydrocarbon solubility of the phosphate esters. This is an important advantage of the present inhibitors since many inhibitors are not hydrocarbon soluble. For example, the salts and quaternaries of the phosphate esters are soluble in hydrocarbon solvents, e.g., benzene, toluene, trimethylbenzene and especially in light condensates ($C_6$–$C_{10}$ hydrocarbon mixtures) which are often used as diluents for inhibitors since they are a well by-product.

In general, a minor but effective amount of the compounds of the present invention is employed to inhibit corrosion in deep gas wells and distribution systems, such as from about 1 to about 10,000 parts per million (ppm), preferably from about 500 to about 5,000 ppm, especially from about 20 to about 2,500 ppm, when added on a continuous basis. Obviously, larger amounts will be used if added on a batch basis.

The following nonlimiting examples are for illustrative purposes only and represent the best mode of practice of the invention.

In the following examples the wheel test is used to determine the efficiency of the corrosion inhibitors. The test allows comparison of compounds. The test procedure is as follows:

Test Procedure

Coupons:
  Grit-blasted coupons of mild steel (179×6×1 mm) were cleaned with methanol, dried in hexane, and weighed.
Medium:
  250 ml bottles were filled with:
  100 ml of kerosene (sparged with $CO_2$)
  100 ml of 3% NaCl in deionized water (sparged with $CO_2$)
  x ppm inhibitor, with respect to kerosene For blank determination, bottles with brine and kerosene in the used volumes, but without inhibitor, were used.

Execution of Experiment

The fluids were saturated separately with $CO_2$. The inhibitors and coupons were placed into the bottles. The bottles were purged with $CO_2$, then filled with the proper amount of each fluid. After placing a blanket of $CO_2$ on the top, the bottles were sealed. They were placed in a rotating bottle cabinet and rotated end-over-end for 24 hours at 77° C.

After 24 hours the coupons were removed and placed in trimethylbenzene to prevent flash rusting. They were then rinsed in (1) water, (2) 10% HCl, (3) water, (4) methanol, and (5) A.C.S. methanol. The coupons were removed from the methanol one at a time and physically dried with a paper towel. The coupons were then reweighed.

Corrosion results were calculated from net weight loss of the coupons. The efficiency of the inhibitor is expressed as the percentage of protection, which is calculated as follows:

$$\% \text{ protection} = \frac{WO - W}{WO} \times 100\%$$

WO = loss of weight of blank
W = loss of weight of inhibited test coupon

Example 1

This example illustrates the preparation of the phosphate ester of the reaction product of isooctyl mercaptan and ethylene oxide. Ethylene oxide and isooctyl mercaptan were reacted, using 1.3 moles ethylene oxide per mole of isooctyl mercaptan, to afford the compound:

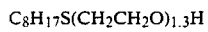

$$C_8H_{17}S(CH_2CH_2O)_{1.3}H$$

which was heated to 50° C. under nitrogen. To the oxyalkylate there was added 0.17 mole $P_2O_5$ under anhydrous conditions at such a rate that the temperature did not exceed about 80° C. After the addition was complete, the temperature was adjusted to 80° C. and maintained for 5 hours. The following approximately equimolar mixture of compounds was afforded:

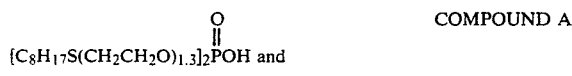

COMPOUND A
$[C_8H_{17}S(CH_2CH_2O)_{1.3}]_2\overset{O}{\overset{\|}{P}}OH$ and

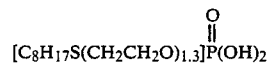

$[C_8H_{17}S(CH_2CH_2O)_{1.3}]\overset{O}{\overset{\|}{P}}(OH)_2$

Examples 2-5

In the same manner as illustrated in Example 1, the oxyethylated mercaptans listed in Table I were phosphated (phosphorous pentoxide) to afford the corresponding phosphate esters.

TABLE I

| EXAMPLE | COMPOUND | MERCAPTAN | MOLES ETHYLENE OXIDE |
|---|---|---|---|
| 2 | B | Octyl | 2 |
| 3 | C | Octyl | 2.7 |
| 4 | D | Octyl | 3.3 |
| 5 | E | Dodecyl | 3 |

Similarly, phosphate esters of the following compounds may be prepared:

| MERCAPTAN | ALKYLENE OXIDE |
|---|---|
| butyl | propylene |
| hexyl | propylene |
| nonyl | butylene |
| tridecyl | ethylene |
| tetradecyl | ethylene |
| octadecyl | ethylene |
| eicosyl | propylene |

Example 6-8

Compounds C, D and E (Examples 3-5) were tested, in accordance with the wheel test described above, in the absence of other materials. The results are set forth in Table II below.

TABLE II

| EXAMPLE | COMPOUND | ESTERS (ppm) | % PROTECTION |
|---|---|---|---|
| 6 | C | 100 | 91 |
| 7 | D | 100 | 22 |
| 8 | E | 50 | 88 |

The data illustrate (1) that excellent inhibition is afforded by the neat compounds and (2) the criticality of the mole ratio of alkylene oxide to mercaptan to afford materials having inhibitory properties.

Examples 9-19

In examples 9-19, Compound B was formulated with various dimer acids, amine salts, surfactants and solvents and the percent protection was determined in accordance with the wheel test procedure. The results are set forth in Table III below.

TABLE III

| | | | BLEND COMPOSITION | | | | | | | | |
|---|---|---|---|---|---|---|---|---|---|---|---|
| EXAM-PLE | COM-POUND | PARTS | AMINE TYPE | PARTS | DIMER ACID | PARTS | SURFACTANT TYPE | PARTS | SOLVENT TYPE | PARTS | ppm | % PROTECTION |
| 9 | B | 2.5 | — | — | c | 2.5 | — | — | — | — | 100 | 95 |
| 10 | B | 2 | a | 2 | c | 2 | f | 0.3 | d | 6.3 | 100 | 84 |
| 11 | B | 5 | — | — | — | — | f | 0.25 | d | 5.25 | 100 | 89 |
| 12 | B | 1 | — | 1 | c | 1 | g | 0.3 | d | 3.3 | 100 | 90 |
| 13 | B | 2 | — | 2 | c | 2 | g | 0.6 | d | 6.6 | 100 | 87 |
| 14 | B | 1 | — | — | c | 1 | f | 0.3 | d/e | 6/1 | 100 | 86 |
| 15 | B | 2 | a | 2 | c | 2 | f | 0.3 | d/e | 6.3/1 | 100 | 64 |
| 16 | B | 2 | — | — | h | 1.5 | f | 0.1 | d/e | 5.9/0.5 | 100 | 93 |
| 17 | B | 1 | — | — | c | 1 | f | 0.3 | d/e | 6.1 | 100 | 91 |
| 18 | B | 5 | a | 2.5 | — | — | — | — | — | — | 100 | 84 |

TABLE III-continued

| EXAMPLE | COMPOUND | PARTS | AMINE TYPE | AMINE PARTS | DIMER ACID | DIMER PARTS | SURFACTANT TYPE | SURFACTANT PARTS | SOLVENT TYPE | SOLVENT PARTS | ppm | % PROTECTION |
|---|---|---|---|---|---|---|---|---|---|---|---|---|
| 19 | B | 5 | a | 2.3 | — | — | — | — | — | — | 100 | 83 | a = morpholine mixture (Jefferson Chem. Co.)
b = morpholine benzyl chloride quaternary (Jefferson Chem. Co.)
c = dimer acids
d = trimethylbenzene
e = butyl carbitol
f = oxyethylated dinonyl phenol
g = dimethyl cocoamine, $H_2O$, $CH_3OH$, benzyl chloride quaternary (Armeen)
h = dimer acids + tall oil fatty acids While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

We claim:

1. The method of inhibiting corrosion of ferrous metals which comprises contacting said metals with an effective amount of an inhibitor having the formula $$[R_1S(R_2O)_x]_m\text{---}P(OH)_n$$
$$\overset{\displaystyle O}{\|}$$

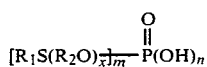

wherein $R_1$ represents alkyl, cycloalkyl, aryl, aralkyl and heterocyclyl; $R_2$ represents alkyl; x represents an integer of from 2 to about 4; m represents an integer which is 1 or 2; n represents the integer 1 when m is 2 and represents 2 when m is 1 and the amine and quaternary ammonium salts thereof.

2. Method of claim 1 wherein $R_1$ is alkyl.

3. Method of claim 1 wherein said inhibitor is in the form of the amine salt thereof.

4. Method of claim 1 wherein $R_1$ is alkyl and said inhibitor is in the form of the amine salt thereof.

5. Method of claim 1 wherein said inhibitor is in the form of a quaternary ammonium salt thereof.

6. Method of claim 1 wherein $R_1$ is alkyl and said inhibitor is in the form of a quaternary ammonium salt thereof.

7. The method of inhibiting corrosion of metals in gas wells and distribution systems therefor which comprises adding thereto an effective amount of an inhibitor having the formula

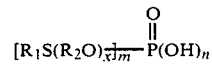

wherein $R_1$ represents alkyl, cycloalkyl, aryl, aralkyl and heterocyclyl; $R_2$ represents alkyl; x represents an integer of from 2 to about 4; m represents an integer which is 1 or 2; n represents the integer 1 when m is 2 and represents 2 when m is 1 and the amine and quaternary ammonium salts thereof.

8. Method of claim 7 wherein said inhibitor is in the form of an amine salt thereof.

9. Method of claim 7 wherein said inhibitor is in the form of a quaternary ammonium salt thereof.

* * * * *